Jan. 30, 1940. C. SALBACH Plant Pat. 360
GLADIOLUS
Filed March 29, 1939
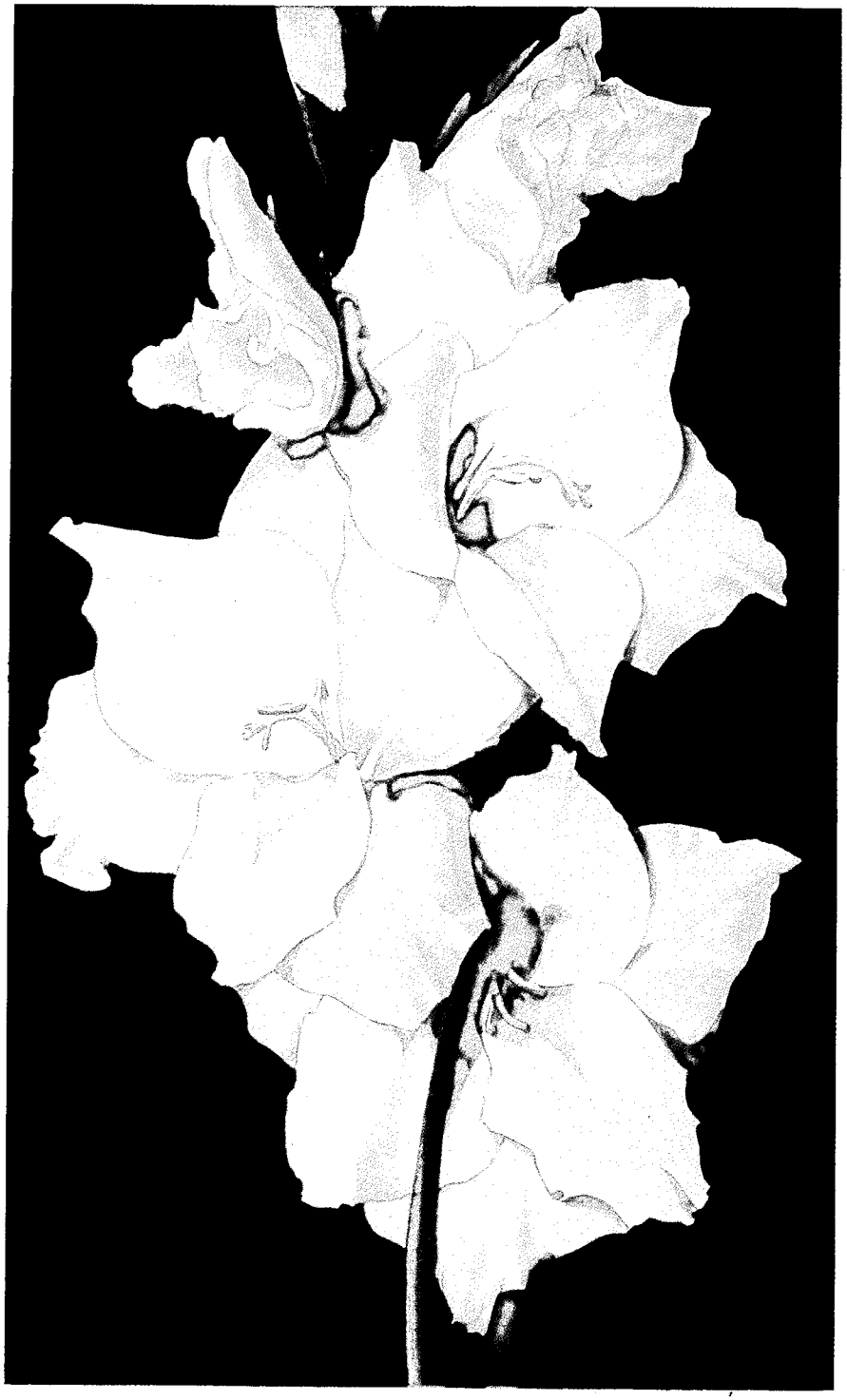
Inventor — Carl Salbach
By Orville M. Kile — Plant Pat. Agt.

Patented Jan. 30, 1940

Plant Pat. 360

UNITED STATES PATENT OFFICE

360

GLADIOLUS

Carl Salbach, Contra Costa County, Calif., assignor to Ella S. Salbach, Contra Costa County, Calif.

Application March 29, 1939, Serial No. 264,807

1 Claim. (Cl. 47—60)

My present invention relates to improvements in flowering gladioli of the type notable for size and quality of bloom. The object of this invention is to provide a superior gladiolus of the coloring commonly referred to as "deep salmon", with very large individual flowers of good quality which are unusually well placed and well formed.

My new variety originated as a seedling produced from cross pollination work carried on by myself, and it is a cross between Grand Opera (the subject of Plant Patent No. 280) as the pollen parent, and Picardy as the seed parent. This variety has been reproduced asexually through several generations and its characteristics appear to be fixed.

The illustration accompanying this application shows a portion of the spike of a plant of this variety with flowers in approximately their true colors but somewhat reduced in size.

Color plate references are to Ridgway's Color Standards and Nomenclature.

Following is a more complete description of the plant and flower of this new variety.

*The plant*

Growth:

Very vigorous grower, tips of spikes usually reaching a height of 48 inches or more in my gardens.

Blooming:

Usually each spike opens five to seven of its very large flowers at one time, and has a total of sixteen or seventeen flowers in all.

Foliage:

Usually 9 to 10 leaves. Tall. Center leaves 12 to 14 inches long and 1½ inches wide. Droop slightly at ends. Oriental Green (Plate XVIII).

Stems:

Stiff and strong. Fully adequate to hold the immense flower spike in an upright position.

Spike:

Unusually long, attaining a length of 26 inches.

Arrangement:

Flowers symmetrically placed, facing in one direction. This is a consistent achievement of my new variety.

Corms:

Exceptionally large. Have good covering.

*The flower*

The blossom:

Consists of six petals of rather uniform size and shape.

*Size.*—The individual flowers usually run from six to seven inches in diameter. Much larger than flowers of varieties of similar color when grown under the same conditions.

*Form.*—The six rather uniform, pointed petals give the flower the form of a six-pointed star.

*Petals.*—Shape—pointed. Substance—heavy, making the variety very valuable for shipping and long keeping. Aspect—smooth and unwrinkled. Color—Light Coral Red (Plate XIII), with a small spit of Carmine (Plate I) at the center. These colors are very rich and soft.

*Stamens.*—The three filaments are white, the anthers being white on the top and covered on the bottom with light colored pollen which appears almost gray.

*Pistils.*—Medium size. Cream Color (Plate XVI) with slight pink tinge. Extend very little farther than the stamens.

*Comparison*

Other known varieties of similar color all have much smaller flowers. Mrs. Leon Douglas, the closest approach to this new variety in similarity, differs in several respects, particularly in that it has much smaller flowers and lacks the consistency of this new variety in producing spikes of bloom where the flowers are all facing in one direction.

The most notable characteristics which in combination readily distinguish my new gladiolus from all other known "deep salmon" or Light Coral Red varieties, particularly Mrs. Leon Douglas, are:

1. The general symmetry and placement of the flowers, and the fact that the plant is consistent in this respect.
2. The usually good shipping and keeping qualities.
3. The richness and softness of color.
4. The vigorous growth and resultant long spikes.
5. The great size of the flowers.
6. The heavy substance of the flowers.

Having thus disclosed my invention, I claim:

The new variety of gladiolus plant herein described and illustrated, characterized particularly by its vigor of growth; its general symmetry; and its consistency in producing well placed flowers of very large size and soft rich Light Coral Red and Carmine coloring as described.

CARL SALBACH.